US008674156B2

(12) United States Patent
Chung et al.

(10) Patent No.: US 8,674,156 B2
(45) Date of Patent: Mar. 18, 2014

(54) MIXED MANGANESE FERRITE CATALYSTS, METHOD OF PREPARING THEREOF AND METHOD OF PREPARING 1,3-BUTADIENE USING THEREOF

(75) Inventors: Young Min Chung, Daejeon (KR); Yong Tak Kwon, Daejeon (KR); Tae Jin Kim, Daejeon (KR); Seong Jun Lee, Daejeon (KR); Min Su Ko, Daejeon (KR); Seung Hoon Oh, Daejeon (KR); Yong Seung Kim, Seoul (KR); In Kyu Song, Seoul (KR)

(73) Assignees: SK Innovation Co., Ltd. (KR); SK Global Chemical Co. Ltd. (KR)

( * ) Notice: Subject to any disclaimer, the term of this patent is extended or adjusted under 35 U.S.C. 154(b) by 456 days.

(21) Appl. No.: 12/746,558

(22) PCT Filed: Nov. 7, 2008

(86) PCT No.: PCT/KR2008/006568
§ 371 (c)(1),
(2), (4) Date: Jun. 7, 2010

(87) PCT Pub. No.: WO2009/075478
PCT Pub. Date: Jun. 18, 2009

(65) Prior Publication Data
US 2010/0280300 A1    Nov. 4, 2010

(51) Int. Cl.
*C07C 5/48*    (2006.01)
*B01J 23/889*    (2006.01)

(52) U.S. Cl.
USPC ........... 585/625; 585/616; 585/617; 585/621; 585/624; 502/324; 502/338

(58) Field of Classification Search
USPC ................. 585/601, 616, 617, 621, 624, 625; 502/324, 338
See application file for complete search history.

(56) References Cited

U.S. PATENT DOCUMENTS 3,420,912 A * 1/1969 Woskow et al. ............... 585/625
3,450,787 A * 6/1969 Kehl et al. ..................... 585/625
(Continued)

FOREIGN PATENT DOCUMENTS

JP         46-2063       10/1971
WO    WO 96/18457       6/1996

OTHER PUBLICATIONS

Obenaus, et al., "Butenes" in Ullmann's Encyclopedia of Industrial Chemistry, 2002, Wiley-VCH, available on-line Jun. 15, 2000.*
(Continued)

*Primary Examiner* — In Suk Bullock
*Assistant Examiner* — Bradley Etherton
(74) *Attorney, Agent, or Firm* — DLA Piper LLP (US)

(57) ABSTRACT

A method of producing a mixed manganese ferrite catalyst, and a method of preparing 1,3-butadiene using the mixed manganese ferrite catalyst. Specifically, a method of producing a mixed manganese ferrite catalyst through a coprecipitation method which is performed at a temperature of 10~40° C., and a method of preparing 1,3-butadiene using the mixed manganese ferrite catalyst through an oxidative dehydrogenation reaction, in which a C4 mixture containing n-butene, n-butane and other impurities is directly used as reactants without performing additional n-butane separation process or n-butene extraction. 1,3-butadiene can be prepared directly using a C4 mixture including n-butane at a high concentration as a reactant through an oxidative hydrogenation reaction without performing an additional n-butane separation process, and 1,3-butadiene, having high activity, can be also obtained in high yield for a long period of time.

11 Claims, 2 Drawing Sheets

(56) References Cited

U.S. PATENT DOCUMENTS

| | | | |
|---|---|---|---|
| 3,567,793 A * | 3/1971 | Coiling et al. | 585/625 |
| 3,671,606 A * | 6/1972 | Manning | 585/625 |
| 3,743,683 A | 7/1973 | Croce et al. | |
| 3,900,525 A * | 8/1975 | Christmann et al. | 585/443 |
| 3,951,869 A | 4/1976 | Baker | |
| 4,097,392 A * | 6/1978 | Goldman et al. | 252/62.62 |
| 4,372,865 A * | 2/1983 | Yu et al. | 252/62.62 |
| 4,658,074 A * | 4/1987 | Bajars et al. | 585/380 |
| 5,689,023 A | 11/1997 | Hamilton, Jr. | |
| 6,391,222 B1 | 5/2002 | Watanabe | |
| 2003/0042470 A1 | 3/2003 | Ishida et al. | |

OTHER PUBLICATIONS

Lide, CRC Handbook of Chemistry and Physics, 91st edition, 2011 Internet Version—month unknown.*

Kolk, et al. "Evidence of a new Structural Phase of Manganese—Iron Oxide" in Hyperfine Interactions (1988), 42(1-4), 1051-1054—Abstract only, month unknown.*

Luis M. Madeira and Manuel F. Portela, "Catalytic Oxidative Dehydrogenation of n-Butane," Marcel Dekker, Inc., 2002, pp. 247-286.

Michael A. Gibson and Joe W. Hightower, Oxidative Dehydrogenation of Butenes Over Magnesium Ferrite Kinetic and Mechanistic Studies, Journal of Catalysts 41, Inc. 1976, pp. 420-430.

W. Ronald Cares and Joe W. Hightower, "Ferrite Spinels as Catalysts in the Oxidative Dehydrogenation of Butenes," Journal of Catalysts 23, 1971, pp. 193-203.

R.J. Rennard and W. L. Kehl, "Oxidative Dehydrogenation ofButenes Over Ferrite Catalysts," Journal of Catalysts 21, pp. 282-293.

Yu M. Bakshi, R. N. Gur'Yanova, A. N. Mal'yan and A. I. Gel'Bshtein, "Catalytic Properties of System $SnO_2:Sb_2O_4$ in the Oxidative Dehydrogenation of n-Butenes to Butadiene," Petroleum Chemistry, USSR, vol. 7, 1967, pp. 177-185.

A. C. A. M. Bleijenberg, B. C. Lippens and G. C. A. Schuit, "Catalytic Oxidatin of 1-Butene over Bismuth Molybdate Catalysts," Journal of Catalysts 4, 1965, pp. 581-585.

Ph. A. Batist, B. C. Lippens, and G. C. A. Schuit, "The Catalytic Oxidation of 1-Butene over Bismuth Molybdate Catalysts," Journal of Catalysts 5, 1965, pp. 55-64.

W. J. Linn and A. W. Sleight, "Oxidation of 1-Butene over Bismuth Molybdates and Bismuth Iron Molybdate," Journal of Catalysts 41, 1976, pp. 134-139.

Feng-yan Qiu, Lu-Tao Weng, E. Sham, P. Ruiz and B. Delmon, Effect of Added $Sb_2O_4$, $BiPO_4$ or $SnO_2$ on the Catalytic Propeorties of $ZnFe_2O_4$ in the Oxidative Dehydrogenation ofButene to Butadiene, Applied Catalysis, 51, 1989, pp. 235-253.

J. A. Toledo, P. Bosch, M. A. Valenzuela, A. Montoya and N. Nava, "Oxidative Dehydrogenation of 1-Butene Over Zn—Al Ferrites," Journal of Molecular Catalysis A: Chemical 125, 1997, pp. 53-62.

Tatsuya Kodama, Masataka Ookubo, Satoshi Miura and Yoshie Kitayama, "Synthesis and Characterization of Ultrafine Mn(II)-Bearing Ferrite of Type $Mn_xFe_{3-x}O_4$ by Coprecipitation," Materials Research Bulletin, vol. 31, No. 12, 1996, pp. 1501-1512.

Z. John Zhang, Zhong L. Wang, Bryan C. Chakoumakos and Jin S. Yin, "Temperature Dependence of Cation Distribution and Oxidation State in Magnetic Mn—Fe Ferrite Nanocrystals," Journal of American Chemical Society, 120, 1998, pp. 1800-1804.

L. Marshall Welch, Louis J. Croce and Harold F. Christmann, "Butadiene Via Oxidative Dehydrogenation," Petrochemical Developments, 1978, pp. 59-.

R. K. Grasselli, "Ammoxidation," Handbook of Heterogeneous Catalysis, vol. 2, 1997, pp. 2302-2326.

Z. X. Tang, et al., "Preparation of Manganese Ferrite Fine Particles from Aqueous Solution," *Journal of Colloid and Interface Science*, Academic Press, New York, NY, Oct. 1, 1991, vol. 146, No. 1, pp. 38-52.

J. Ding, et al., "Formation of Spinel Mn-Ferrite During Mechanical Alloying," *Journal of Magnetism and Magnetic Materials*, Elsevier Science Publishers, Amsterdam, NL, Jul. 1, 1997, vol. 171, No. 3, pp. 309-314.

Zhang Bianfang, et al., "Synthesis of Magnetic Manganese Ferrite," Journal of Wuhan University of Technology—Materials Science Edition, Sep. 2007, vol. 22, No. 3, pp. 514-517.

* cited by examiner

MIXED MANGANESE FERRITE CATALYSTS, METHOD OF PREPARING THEREOF AND METHOD OF PREPARING 1,3-BUTADIENE USING THEREOF

RELATED APPLICATIONS

This is a §371 of International Application No. PCT/KR2008/006568, with an international filing date of Nov. 7, 2008 (WO 2009/075478 A2, published Jun. 18, 2009), which is based on Korean Patent Application No. 10-2007-0129115 filed Dec. 12, 2007.

TECHNICAL FIELD

The present disclosure relates to a mixed manganese ferrite catalyst, a method of producing the same, and a method of preparing 1,3-butadiene using the same. Specifically, the present disclosure relates to a method of producing a mixed manganese ferrite catalyst through a coprecipitation method which is performed at a temperature of 10~40° C., and to a method of preparing 1,3-butadiene using the mixed manganese ferrite catalyst through an oxidative dehydrogenation reaction, in which a cheap C4 mixture containing n-butene, n-butane and other impurities is directly used as reactants without performing additional n-butane separation process or n-butene extraction.

BACKGROUND 1,3-butadiene, the demand for which is increasing in petrochemical markets, is produced through a naphtha cracking process, a direct n-butene dehydrogenation reaction, or an oxidative n-butene dehydrogenation reaction, and is then supplied to the petrochemical market. Among them, the naphtha cracking process accounts for 90% or more of butadiene supply, but is problematic in that new naphtha cracking centers (NCCs) must be established in order to meet the increasing demand for butadiene, and in that other basic petrochemical raw materials besides butadiene are excessively produced because the naphtha cracking process is not a process for producing only butadiene. Further, the direct dehydrogenation reaction of n-butene is problematic in that it is thermodynamically disadvantageous, and in that high-temperature and low-pressure conditions are required because it is an endothermic reaction, so that the yield is very low, with the result that it is not suitable as a commercial process [L. M. Madeira, M. F. Portela, Catal. Rev., volume 44, page 247 (2002)].

The oxidative dehydrogenation reaction of n-butene, which is a reaction for forming 1,3-butadiene and water by reacting n-butene with oxygen, is advantageous in that stable water is formed as a product, so that the reaction is thermodynamically favorable and the reaction temperature can be lowered. Therefore, a process of producing 1,3-butadiene through the oxidative dehydrogenation reaction of n-butene can be an effective alternative process for producing only butadiene. In particular, when a C4-raffinate-3 mixture or a C4 mixture containing impurities, such as n-butane and the like, is used as the supply source of n-butene, there is an advantage in that excess C4 fractions can be made into high value-added products. Specifically, the C4-raffinate-3 mixture, which is a reactant used in the present invention, is a cheap C4 fraction obtained by separating useful compounds from a C4 mixture produced through naphtha cracking. More specifically, a C4-raffinate-1 mixture is a mixture obtained by separating 1,3-butadiene from a C4 mixture produced through naphtha cracking, a C4-raffinate-2 mixture is a mixture obtained by separating iso-butylene from the C4-raffinate-1 mixture, and a C4-raffinate-3 mixture is a mixture obtained by separating 1-butene from the C4-raffinate-2 mixture. Therefore, the C4-raffinate-3 mixture or C4 mixture mostly includes 2-butene (trans-2-butene and cis-2-butene), n-butane, and 1-butene.

As described above, the oxidative dehydrogenation reaction of n-butene (1-butene, trans-2-butene, cis-2-butene) is a reaction for forming 1,3-butadiene and water by reacting n-butene with oxygen. However, in the oxidative dehydrogenation reaction of n-butene, many side reactions such as complete oxidation etc. are predicted because oxygen is used as a reactant. For this reason, it is very important to develop a catalyst which can suppress these side reactions to the highest degree possible and which has high selectivity for 1,3-butadiene. Examples of catalysts currently used for the oxidative dehydrogenation reaction of n-butene include a ferrite-based catalyst [M. A. Gibson, J. W. Hightower, J. Catal., volume 41, page 420 (1976)/W. R. Cares, J. W. Hightower, J. Catal., volume 23, page 193 (1971)/R. J. Rennard, W. L. Kehl, J. Catal., volume 21, page 282 (1971)], a tin-based catalyst [Y. M. Bakshi, R. N. Gur'yanova, A. N. Mal'yan, A. I. Gel'bshtein, Petroleum Chemistry U.S.S.R., volume 7, page 177 (1967)], a bismuth molybdate-based catalyst [A. C. A. M. Bleijenberg, B. C. Lippens, G. C. A. Schuit, J. Catal., volume 4, page 581 (1965)/Ph. A. Batist, B. C. Lippens, G. C. A. Schuit, J. Catal., volume 5, page 55 (1966)/W. J. Linn, A. W. Sleight, J. Catal., volume 41, page 134 (1976)/R. K. Grasselli, Handbook of Heterogeneous Catalysis, volume 5, page 2302 (1997)] and the like.

Among them, the ferrite-based catalyst has a spinel structure of $AFe_2O_4$ (A=Zn, Mg, Mn, Co, Cu, and the like). It is known that the ferrite having such a spinel structure can be used a catalyst for an oxidative dehydrogenation reaction through the oxidation and reduction of iron ions and the interaction of oxygen ions and gaseous oxygen in crystals [M. A. Gibson, J. W. Hightower, J. Catal., volume 41, page 420 (1976)/R. J. Rennard, W. L. Kehl, J. Catal., volume 21, page 282 (1971)]. The catalytic activities of ferrite-based catalysts are different from each other depending on the kind of metals constituting the bivalent cation sites of the spinel structure. Among them, zinc ferrite, magnesium ferrite and manganese ferrite are known to exhibit good catalytic activity in the oxidative dehydrogenation reaction of n-butene, and, particularly, zinc ferrite is reported to have higher selectivity for 1,3-butadiene than do other metal ferrites [F.-Y. Qiu, L.-T. Weng, E. Sham, P. Ruiz, B. Delmon, Appl. Catal., volume 51, page 235 (1989)].

It was reported in several patent documents that zinc ferrite-based catalysts were used in the oxidative dehydrogenation reaction of n-butene. Specifically, concerning the production of 1,3-butadiene through the oxidative dehydrogenation reaction of n-butene using pure zinc ferrite made by a coprecipitation method, it was reported that the oxidative dehydrogenation reaction of 2-butene was conducted at 375° C. using a zinc ferrite catalyst having a pure spinel structure, thus obtaining a yield of 41% [R. J. Rennard, W. L. Kehl, J. Catal., volume 21, page 282 (1971)]. Further, it was reported that 1,3-butadiene was obtained at a yield of 21% at 420° C. through an oxidative dehydrogenation reaction, in which 5 mol % of 1-butene was used as a reactant and a zinc ferrite catalyst was used [J. A. Toledo, P. Bosch, M. A. Valenzuela, A. Montoya, N. Nava, J. Mol. Catal. A, volume 125, page 53 (1997)].

Further, methods of manufacturing a zinc ferrite catalyst, by which 1,3-butadiene can be produced in higher yield for a long period of time through pre-treatment and post-treatment conducted in order to increase the activity and lifespan of a zinc ferrite catalyst in an oxidative dehydrogenation reaction, was disclosed in several patent documents [F.-Y. Qiu, L.-T. Weng, E. Sham, P. Ruiz, B. Delmon, Appl. Catal., volume 51, page 235 (1989)/L. J. Crose, L. Bajars, M. Gabliks, U.S. Pat. No. 3,743,683 (1973)/J. R. Baker, U.S. Pat. No. 3,951,869 (1976)].

It was reported in several patent documents that, in addition to the above zinc ferrite catalyst, manganese ferrite-based catalysts were used in the oxidative dehydrogenation reaction of n-butene. Specifically, when 1,3-butadiene is produced through the oxidative dehydrogenation reaction of n-butene using a pure manganese ferrite catalyst made by a coprecipitation method and a physical mixing method, it was reported that 1,3-butadiene was obtained at a yield of 51% at 475° C. through an oxidative dehydrogenation reaction, in which 2-butene was used as a reactant and the manganese ferrite catalyst was used [P. M. Colling, J. C. Dean, U.S. Pat. No. 3,567,793 (1971)/H. E. Manning, U.S. Pat. No. 3,671,606 (1972)].

In the oxidative dehydrogenation of n-butene, the above-mentioned zinc ferrite catalyst is problematic in that metal oxides must be added in order to prevent inactivation, acid treatment must be conducted and complicated post treatment procedures are required; and the manganese ferrite catalyst is problematic in that high temperature must be maintained during coprecipitation in order to produce a manganese ferrite catalyst having a pure spinel structure and the yield of 1,3-butadiene obtained using the manganese ferrite catalyst is lower than that obtained using the zinc ferrite catalyst [refer to H. E. Manning, U.S. Pat. No. 3,671,606 (1972)/T. Kodama, M. Ookubo, S. Miura, Y. Kitayama, Mater. Res. Bull., volume 31, page 1,501 (1996)/Z. J. Zhang, Z. L. Wang, B. C. Chakoumakos, J. S. Yin, J. Am. Chem. Soc., volume 120, page 1,800 (1998)].

The oxidative dehydrogenation reaction of n-butene has another problem in that, when a reactant includes a predetermined quantity or greater of n-butane, the yield of 1,3-butadiene is decreased [L. M. Welch, L. J. Croce, H. F. Christmann, Hydrocarbon Processing, page 131 (1978)]. Therefore, in the above conventional technologies, an oxidative dehydrogenation reaction is conducted using only pure n-butene (1-butene or 2-butene) as a reactant, thus solving such a problem. In practice, reactants containing no n-butane are used even in commercial processes using a ferrite catalyst. As disclosed in the above patent documents, in the catalytic process for preparing 1,3-butadiene from n-butene through an oxidative dehydrogenation reaction, since pure n-butene is used as a reactant, an additional process of separating pure n-butene from a C4 mixture is required, thus inevitably decreasing economic efficiency.

SUMMARY

Therefore, in order to overcome the above problems, the present inventors found that, when a mixed manganese ferrite catalyst, produced through a coprecipitation method which is performed at a temperature of 10~40° C., is used, 1,3-butadiene can be prepared in high yield on the mixed manganese ferrite catalyst using a cheap C4 mixture including n-butane and n-butene as a reactant through an oxidative dehydrogenation reaction without performing an additional n-butene separation process. Based on these findings, the present disclosure was completed.

Accordingly, the present disclosure has been made keeping in mind the above problems occurring in the prior art, and an aspect of the present disclosure is to provide a method of producing a mixed manganese ferrite catalyst for preparing 1,3-butadiene in high yield, in which the mixed manganese ferrite catalyst has excellent catalytic activity, and can be easily synthesized and reproduced because additional processes for improving the activity of the catalyst and increasing the lifespan thereof are not required.

Another aspect of the present disclosure is to provide a method of preparing 1,3-butadiene in high yield by performing an oxidative dehydrogenation reaction on the mixed manganese ferrite catalyst produced through the method of the present disclosure by directly using a cheap C4 mixture as a reactant without performing an additional n-butene separation process.

In order to accomplish the above, an aspect of the present disclosure provides a method of producing a mixed manganese ferrite catalyst for preparing 1,3-butadiene, including: (A) providing an aqueous precursor solution including a manganese precursor and an iron precursor, in which atom ratio of iron (Fe) to manganese (Mn) is 1.8~2.4; (B) mixing the aqueous precursor solution with an alkaline solution having a molar concentration of 1.5~4.0 M at a temperature of 10~40° C. to form a coprecipitated solution; (C) washing and filtering the coprecipitated solution to obtain a solid catalyst; (D) drying the solid catalyst at 70~200° C.; and (E) heat-treating the dried solid catalyst at 350~800° C.

Another aspect of the present disclosure provides a method of preparing 1,3-butadiene using the mixed manganese ferrite catalyst, including: (A) providing a mixed gas of a C4 mixture, air and steam as a reactant; (B) continuously passing the reactant through a catalyst layer supported with the catalyst produced using the method to conduct an oxidative dehydrogenation reaction; and (C) obtaining 1,3-butadiene from the catalyst layer.

According to the present disclosure, a mixed manganese ferrite catalyst, having a simple structure and synthesis procedure and high reproducibility, can be obtained. When the mixed manganese ferrite catalyst is used, 1,3-butadiene can be prepared directly using a C4 mixture including n-butane at a high concentration as a reactant through an oxidative dehydrogenation reaction without performing an additional n-butane separation process, and 1,3-butadiene, having high activity, can be also obtained in high yield for a long period of time.

Further, according to the present disclosure, since 1,3-butadiene, which is highly useful in the petrochemical industry, can be prepared from a C4 mixture or a C4 raffinate-3 mixture, which is of little use, a C4 fraction can be highly value-added. In addition, a process for producing only 1,3-butadiene without newly establishing a naphtha cracking center (NCC) can be secured, so that the demand for 1,3-butadiene can be met, thereby improving economic efficiency compared to conventional processes.

DETAILED DESCRIPTION

Figure 1:
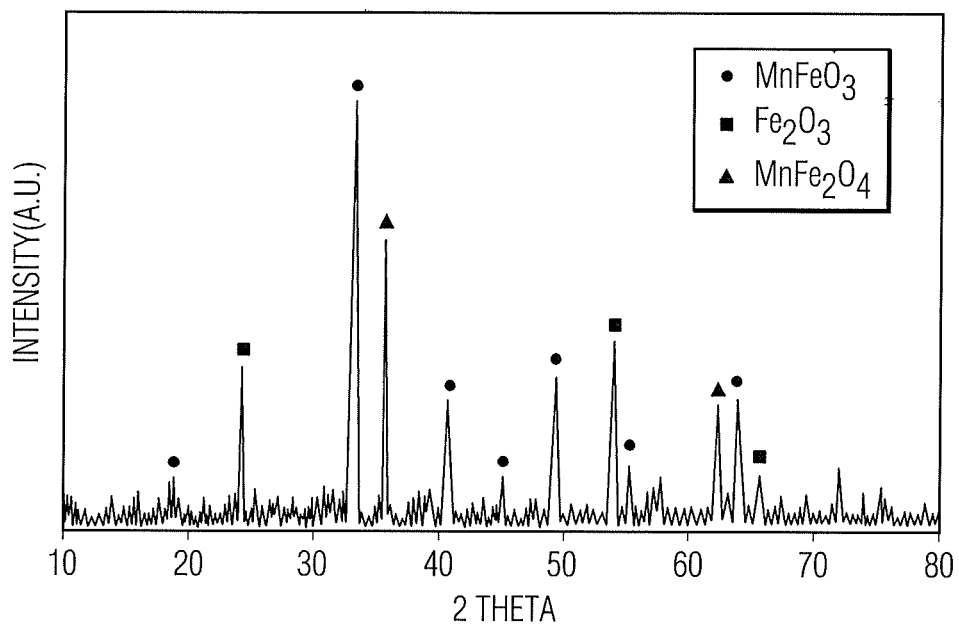
FIG. 1 is a graph showing the results of X-ray diffraction analysis of one kind of mixed manganese ferrite catalyst according to Preparation Example 1 of the present disclosure.

Hereinafter, the present disclosure will be described in detail.

As described above, the present disclosure provides a method of producing a mixed manganese ferrite catalyst through a coprecipitation method which is performed at a temperature of 10~40° C., preferably, 15~30° C., and a method of preparing 1,3-butadiene through the oxidative dehydrogenation of n-butene using the produced mixed manganese ferrite catalyst. In the method of preparing 1,3-butadiene, 1,3-butadiene can be prepared using a C4 mixture as a reactant without performing an additional n-butane separation process.

A mixed manganese ferrite catalyst of the present disclosure is used as a catalyst for preparing 1,3-butadiene in high yield through the oxidative dehydrogenation reaction of n-butene. Since the mixed manganese ferrite catalyst can be produced through simple processes, it can be easily reproduced. Further, the mixed manganese ferrite catalyst of the present invention exhibits high activity in the oxidative dehydrogenation reaction of n-butene, compared to a pure manganese ferrite having a spinel structure.

Chloride precursors and nitrate precursors, which are easily dissolved in distilled water used as a solvent, may be used as a manganese precursor and an iron precursor for preparing the mixed manganese ferrite catalyst. Specifically, the iron precursor may be selected from the group consisting of ferrous chloride tetrahydrate, ferrous chloride hexahydrate, ferrous chloride dihydrate, ferric chloride hexahydrate, ferrous nitrate hexahydrate, ferrous nitrate nonahydrate, ferric nitrate hexahydrate and ferric nitrate nonahydrate, and the manganese precursor may be selected from the group consisting of manganous chloride, manganous chloride tetrahydrate, manganic chloride, manganese tetrachloride, manganese nitrate hexahydrate, manganese nitrate tetrahydrate and manganese nitrate monohydrate.

The amount of the manganese precursor and iron precursor is adjusted such that atom ratio (Fe/Mn) of iron (Fe) to manganese (Mn) is 1.8~2.4. Subsequently, the manganese precursor and iron precursor are each dissolved in distilled water and then mixed with each other to form an aqueous precursor solution. In this case, when the atom ratio of iron (Fe) to manganese (Mn) deviates from the range of 1.8~2.4, manganese cannot easily infiltrate into an iron lattice, or catalytic activity becomes low.

Meanwhile, in order to coprecipitate the manganese and iron precursors at room temperature, an alkaline solution having a molar concentration of 1.5~4.0 M, for example, an aqueous sodium hydroxide solution having a molar concentration of 3 M, is additionally prepared. When the molar concentration of the alkaline solution is below 1.5 M, it is difficult to form a mixed manganese ferrite structure, and when the molar concentration thereof is above 4.0 M, it is difficult to remove metal ions bonded with hydroxide groups, for example, sodium (Na) ions in the case of sodium hydroxide at the time of washing, thus decreasing catalytic activity. As pertains to the formation of the mixed manganese ferrite catalyst structure and post treatment that the molar concentration of the alkaline solution may be adjusted in a range of 2~3 M. As the alkaline solution used to coprecipitate the manganese precursor and iron precursor, other alkaline solutions including ammonia water in addition to the aqueous sodium hydroxide solution may be used. Meanwhile, the alkaline solution exhibits a pH of 9~14.

The aqueous precursor solution including the manganese and iron precursors is injected into the alkaline solution at a temperature of 10° C.~40° C. in order to obtain mixed manganese ferrite from the manganese and iron precursors. In this case, in order to sufficiently coprecipitate the manganese and iron precursors, the aqueous precursor solution and alkaline solution are stirred for 2~12 hours (preferably 6~12 hours) to form a precipitated solution.

Here, when the coprecipitation of the manganese and iron precursors is conducted at less than 10° C., the manganese and iron precursors are not sufficiently coprecipitated, so that extremely unstable bonds are formed, thereby causing side reactions which cannot be easily controlled at the time of using a catalyst. Further, when the coprecipitation thereof is conducted at more than 40° C., catalytic activity is deteriorated, which is not preferable. Therefore, it is preferred that the coprecipitation thereof be conducted at a temperature of 15~30° C., more preferably 15~25° C.

The stirred precipitated solution is sufficiently phase-separated in order to precipitate a solid catalyst, and then the phase-separated precipitated solution is washed and then filtered using a vacuum filter to obtain a solid precipitate sample.

The obtained solid precipitate sample is dried at a temperature of 70~200° C., preferably 120~180° C., for 24 hours. Subsequently, the dried solid precipitate sample is put into an electric furnace, and then heat-treated at a temperature of 350~800° C., preferably 500~700° C., to produce a mixed manganese ferrite catalyst.

Figure 2:
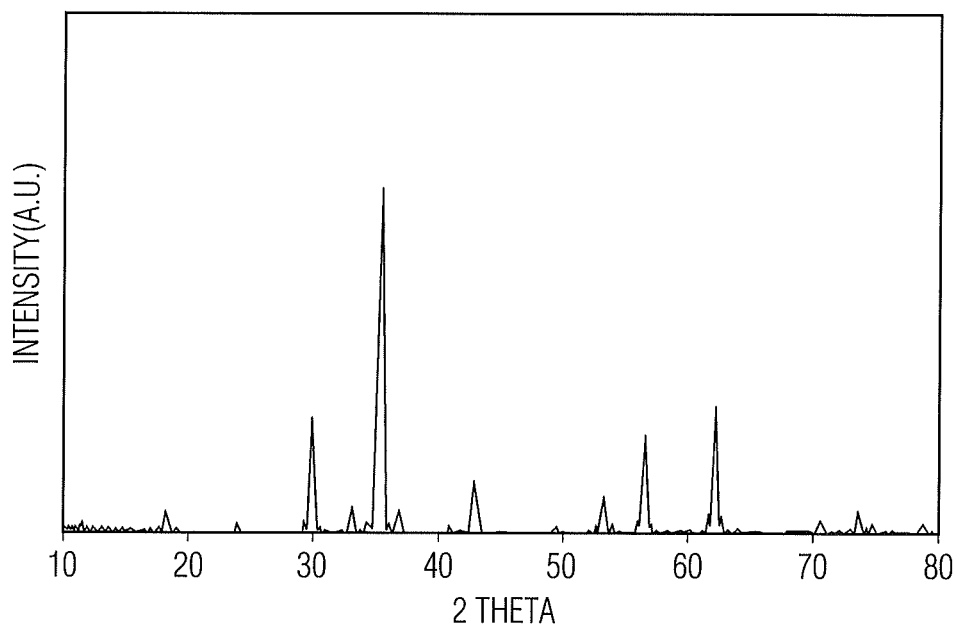
FIG. 2 is a graph showing the results of X-ray diffraction analysis of one kind of zinc ferrite catalyst according to Preparation Example 2 of the present disclosure.

According to Preparation Example 1 of the present disclosure, as a result of comparing the phase characteristics of the catalyst samples produced using a coprecipitation method at room temperature through X-ray diffraction analysis, it was found that mixed manganese ferrite including iron oxide ($\alpha$-$Fe_2O_3$) and manganese iron oxide ($MnFeO_3$), not single-phase manganese ferrite, was formed (referring to FIG. 1). In contrast, it was found that, in the case of the respective catalysts produced in Preparation Examples 2 and 3, single-phase zinc ferrite and single-phase manganese ferrite were formed (referring to FIGS. 2 and 3).

Therefore, the catalyst for preparing 1,3-butadiene according to the present disclosure is a mixed manganese ferrite catalyst which can be conveniently produced at room temperature without performing additional pre-treatment and post-treatment processes and which has high reproducibility.

The mixed manganese ferrite catalyst according to the present disclosure may have peaks in 2-theta ranges of 18.78~18.82, 24.18~24.22, 33.2~33.24, 35.64~35.68, 40.9~40.94, 45.22~45.26, 49.56~49.6, 54.22~54.26, 55.24~55.28, 57.92~57.96, 62.56~62.6, 64.04~64.08, 66.02~66.06, 72.16~72.2 and 75.78~75.82 in X-ray diffraction analysis. And among these peaks, the most salient peak is seen in the 2-theta range of 33.2~33.24.

Further, the present disclosure provides a method of preparing 1,3-butadiene using a C4 mixture or a C4-raffinate-3 mixture on the mixed manganese ferrite catalyst formed by a coprecipitation process at room temperature through an oxidative dehydrogenation reaction without performing an additional n-butane separation process for supplying n-butene.

According to Experimental Example 1 of the present disclosure, a catalytic reaction is conducted by fixing catalyst powder in a linear stainless reactor, and installing the linear stainless reactor in an electric furnace, thus maintaining the reaction temperature of the catalyst layer constant, and then continuously passing reactants through the catalyst layer provided in the linear stainless reactor.

The reaction temperature for conducting an oxidative dehydrogenation reaction is maintained at 300~600° C., preferably 350~500° C., and more preferably 400° C. The amount of the catalyst is set such that the gas hourly space velocity (GHSV) of the reactant is 1~3 h$^{-1}$, preferably 1~2 h$^{-1}$, and more preferably 1.5 h$^{-1}$, based on n-butene. The reactant is a mixed gas of a C4 mixture, air and steam, and the mixing volume ratio of C4 mixture:air:steam in the reactant is 1:0.5~10:1~50, and preferably 1:2~4:10~30. When the mixing volume ratio thereof deviates from this range, desired butadiene yield cannot be obtained, and safety problems may occur due to a rapid exothermic reaction, which is undesirable.

In the present disclosure, n-butene and oxygen, which are reactants for the oxidative dehydrogenation reaction, are supplied in the form of mixed gas. A C4 mixture or a C4-raffinate-3 mixture, which is a supply source of n-butene, is supplied using a piston pump, and air, which is another reactant, is supplied in precisely adjusted amounts using a mass flow controller. Steam, known to be effective in removing the reaction heat caused by the oxidative dehydrogenation reaction and improve selectivity for 1,3-butadiene, is supplied into a reactor by injecting liquid-phase water using a mass flow controller and simultaneously vaporizing it. That is, the temperature of a water inlet in the reactor is maintained at 300~450° C., and preferably 350~450° C., so that the water injected into the reactor using the mass flow controller is immediately vaporized, with the result that the vaporized water is mixed with other reactants (C4 mixture and air) and simultaneously passes through a catalyst layer in the reactor.

Among the reactants of the present disclosure, the C4 mixture includes 0.5~50 wt % of n-butane, 40~99 wt % of n-butene, and 0.5~10 wt % of a balance thereof, which is a C4 mixture other than the n-butane and n-butene. Examples of constituents of the balance include iso-butane, cyclobutane, methyl cyclobutane, iso-butene, and the like.

When the mixed manganese ferrite catalyst of the present disclosure is used, 1,3-butadiene can be produced in high yield from n-butene included in a reactant by performing the oxidative dehydrogenation reaction using a cheap C4 mixture or C4-raffinate-3 mixture including n-butene as the reactant. In particular, even when a C4 mixture including a large amount of n-butane, known to suppress the oxidative dehydrogenation reaction of n-butene, is directly used as a reactant, high activity and high selectivity for 1,3-butadiene can be obtained.

Further, the present disclosure is advantageous in that the mixed manganese ferrite catalyst of the present disclosure is prepared using a direct catalyst synthesis technology, rather than subsidiary technologies, such as conventional catalytic substitution or catalytic treatment, so that the composition of the mixed manganese ferrite catalyst and the synthesis procedure thereof are simple, with the result that the mixed manganese ferrite catalyst is easily synthesized, and 1,3-butadiene can be produced from a C4 mixture or C4-raffinate-3 mixture containing impurities in high yield.

Hereinafter, the present disclosure will be described in more detail with reference to the following Examples, but the scope of the present disclosure is not limited thereto.

Preparation Example 1

Production of Mixed Manganese Ferrite Catalyst

In order to produce a mixed manganese ferrite catalyst, manganese chloride tetrahydrate (MnCl$_2$.4H$_2$O) was used as a manganese precursor, and iron chloride hexahydrate (FeCl$_3$.6H$_2$O) was used as an iron precursor. Both of the manganese precursor and iron precursor are materials easily dissolved in distilled water. 198 g of manganese chloride tetrahydrate and 541 g of iron chloride hexahydrate were dissolved in distilled water (1000 ml), mixed with each other and then sufficiently stirred to form an aqueous precursor solution. Subsequently, after it was confirmed that the precursors were completely dissolved in distilled water, the aqueous precursor solution was dropped onto an aqueous sodium hydroxide solution (6000 ml having a concentration of 3 M at a constant rate to form a mixed solution. The mixed solution was sufficiently stirred using a magnetic stirrer at room temperature for 12 hours, and was then left at room temperature for 12 hours for phase separation. Subsequently, the stirred and left mixed solution was washed using a sufficient amount of distilled water and then filtered using a pressure-sensitive filter to obtain a solid sample, and the obtained solid sample was dried at 160° C. for 24 hours. The dried solid sample was heat-treated in an electric furnace at a temperature of 650° C. for 3 hours under an air atmosphere, thus producing a mixed-phase manganese ferrite catalyst. The phase of the produced catalyst was confirmed through X-ray diffraction analysis based on the following conditions, and the results thereof are shown in Table 1 and FIG. 1. From Table 1 and FIG. 1, it can be seen that the catalyst produced at room temperature is a mixed manganese ferrite catalyst including iron oxide ($\alpha$-Fe$_2$O$_3$) and manganese iron oxide (MnFeO$_3$).

<X-Ray Diffraction Analysis Conditions>
X-ray generator: 3 kW, Cu—K$\alpha$ ray ($\lambda$=1.54056 Å)
Tube voltage: 40 kV
Tube current: 40 mA
2-Theta measurement range: 5 deg~90 deg
Sampling width: 0.02 deg
Scanning rate: 5 deg of 2-Theta/min
Divergence slit: 1 deg
Scattering slit: 1 deg
Receiving slit: 0.15 mm

TABLE 1

Results of X-ray diffraction analysis of mixed-phase manganese ferrite catalyst

| 2 Theta |
| --- |
| 18.8 |
| 24.2 |
| 33.22 |
| 35.66 |
| 40.92 |
| 45.24 |
| 49.58 |
| 54.24 |
| 55.26 |
| 57.94 |
| 62.58 |
| 64.06 |
| 66.06 |
| 72.18 |
| 75.80 |

Preparation Example 2

Production of Zinc Ferrite Catalyst

A single phase zinc ferrite catalyst was produced using the same method as in Preparation Example 1, except that 136 g of zinc chloride (ZnCl$_2$) was used as a zinc precursor instead of the manganese precursor. From FIG. 2, it can be seen through X-ray diffraction analysis that the catalyst produced in Preparation Example 2 is a single phase zinc ferrite catalyst.

Preparation Example 3

Production of Single Phase Manganese Ferrite Catalyst

A single phase manganese ferrite catalyst was produced using the same method as in Preparation Example 1, except that the coprecipitation temperature was maintained at 70° C. and baking temperature was maintained at 475° C. The results of X-ray diffraction analysis of the catalyst produced in Preparation Example 3 are shown in FIG. 3

Figure 3:
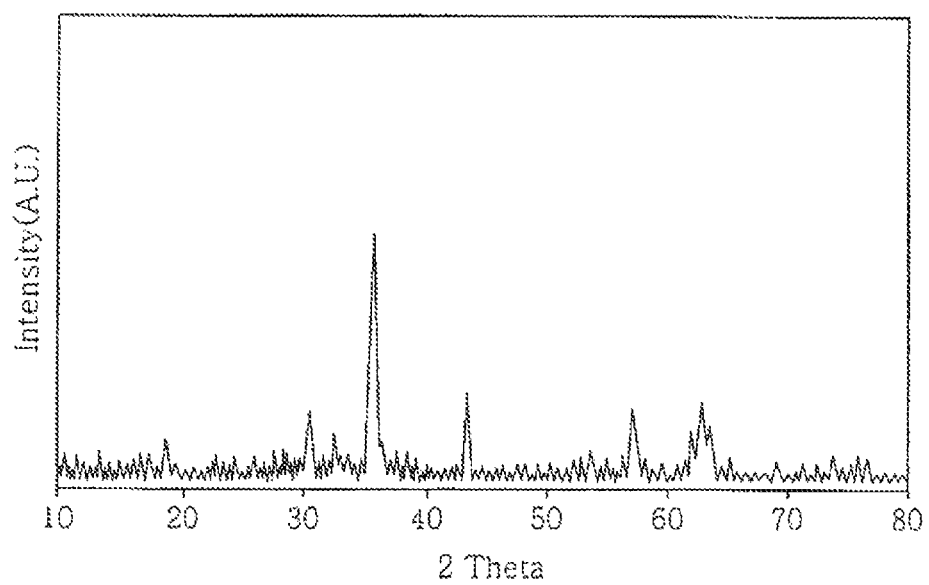
FIG. 3 is a graph showing the results of X-ray diffraction analysis of one kind of pure manganese ferrite catalyst according to Preparation Example 3 of the present disclosure.

From FIG. 3, it can be seen that the catalyst produced in Preparation Example 3 is a single phase manganese ferrite catalyst.

Example 1

Oxidative Dehydrogenation Reaction of C4-Raffinate-3 Mixture or C4 Mixture on Mixed Manganese Ferrite Catalyst The oxidative dehydrogenation reaction of n-butene was conducted using the mixed manganese ferrite catalyst produced in Preparation Example 1 under the following experimental conditions.

In the present disclosure, a C4 mixture was used as a reactant in the oxidative dehydrogenation reaction of n-butene, and the composition thereof is shown in Table 2. The C4 mixture, which is a reactant, was introduced into a reactor in the form of mixed gas together with air and steam, and a linear stainless fixed-bed reactor was used as the reactor.

The composition ratio of the reactant was set based on the amount of n-butene in the C4 mixture, and was set such that the mixing ratio of n-butene:air:steam was 1:3:20. Steam, which was formed by vaporizing liquid-phase water at 350° C., was mixed with other reactants, such as the C4 mixture and air, and then introduced into the reactor. The amount of the C4 mixture was controlled using a piston pump, and the amount of air and steam was controlled by a mass flow controller.

The oxidative dehydrogenation reaction of n-butene was conducted by setting the amount of catalyst such that the liquid hourly space velocity (LHSV), as the flow rate of the reactant, was 1.5 $h^{-1}$, based on the amount of n-butene in the C4 mixture, and the temperature of the catalyst layer in the fixed-bed reactor, as a reaction temperature, was maintained at 400° C. The product obtained after the reaction included carbon dioxide which is a side-product obtained through complete oxidation, side-products obtained through cracking, side-products obtained through isomerization, and n-butane included in the reactant, in addition to the targeted 1,3-butadiene. The product was analyzed using gas chromatography. In the oxidative dehydrogenation reaction of n-butene, the conversion rate of n-butene, selectivity for 1,3-butadiene and yield of 1,3-butadiene through the mixed manganese ferrite catalyst were calculated using the following Mathematical Formulae, respectively.

$$\text{Conversion rate}(\%) = \frac{\text{Number of moles of reacted } n\text{-butene}}{\text{Number of moles of supplied } n\text{-butene}} \times 100 \quad \text{Mathematical Formula 1}$$

$$\text{Selectivity}(\%) = \frac{\text{Number of moles of formed 1,3-butadiene}}{\text{Number of moles of reacted } n\text{-butene}} \times 100 \quad \text{Mathematical Formula 2}$$

$$\text{Yield}(\%) = \frac{\text{Number of moles of formed 1,3-butadiene}}{\text{Number of moles of supplied } n\text{-butene}} \times 100 \quad \text{Mathematical Formula 3}$$

TABLE 2

| Composition of C4 mixture used as reactant | | |
|---|---|---|
| Composition | Molecular formulae | Wt % |
| i-butane | $C_4H_{10}$ | 0 |
| n-butane | $C_4H_{10}$ | 26.8 |
| methyl cyclopropane | $C_4H_8$ | 0.1 |
| trans-2-butene | $C_4H_8$ | 44.1 |
| 1-butene | $C_4H_8$ | 6.6 |
| isobutylene | $C_4H_8$ | 0 |
| cis-2-butene | $C_4H_8$ | 21.9 |
| cyclobutane | $C_4H_8$ | 0.5 |
| i-pentane | $C_5H_{12}$ | 0 |
| total | | 100.00 |

Experimental Example 1

Activity of Mixed Manganese Ferrite Catalyst, Single Phase Zinc Ferrite Catalyst and Single Phase Manganese Ferrite Catalyst The catalysts produced in Preparation Examples 1 to 3 were applied to the oxidative dehydrogenation of a C4 mixture as in Example 1, and the results thereof are shown in Table 3. When the mixed manganese ferrite catalyst produced in Preparation Examples 1 was used, 100 hours after the oxidative dehydrogenation reaction, the conversion rate of n-butene was 68%, the selectivity for 1,3-butadiene was 90%, and the yield of 1,3-butadiene was 61.2%. Further, 1000 hours after the oxidative dehydrogenation reaction, the conversion rate of n-butene was 70%, the selectivity for 1,3-butadiene was 91.5%, and the yield of 1,3-butadiene was 64%. From these results, it can be seen that, when a mixed manganese ferrite catalyst is used, even 1000 hours or more after the oxidative dehydrogenation reaction, the catalyst is not inactivated, and the activity thereof is maintained high for a long period of time.

TABLE 3

| Preparation Examples | Conversion rate of n-butene (%) | | Selectivity for 1,3-butadiene (%) | | Yield of 1,3-butadiene (%) | |
|---|---|---|---|---|---|---|
| | 100 hours after reaction | 1000 hours after reaction | 100 hours after reaction | 1000 hours after reaction | 100 hours after reaction | 1000 hours after reaction |
| 1 | 68 | 70 | 90 | 91.5 | 61.2 | 64.05 |
| 2* | 60 | 54 | 92 | 92 | 55.2 | 49.7 |
| 3* | 62 | 63 | 80 | 80 | 49.6 | 50.4 |

*Comparative Preparation Example

The foregoing examples are provided merely for the purpose of explanation and are in no way to be construed as limiting. While reference to various embodiments are shown, the words used herein are words of description and illustration, rather than words of limitation. Further, although reference to particular means, materials, and embodiments are shown, there is no limitation to the particulars disclosed herein. Rather, the embodiments extend to all functionally equivalent structures, methods, and uses, such as are within the scope of the appended claims.

The invention claimed is:

1. A method of producing a mixed manganese ferrite catalyst for preparing 1,3-butadiene, comprising:
   (A) providing an aqueous precursor solution including a manganese precursor and an iron precursor, in which atom ratio of iron (Fe) to manganese (Mn) is 1.8~2.4;
   (B) mixing the aqueous precursor solution with an alkaline solution having a molar concentration of 1.5~4.0 M at a temperature of 10~40° C. to form a coprecipitated solution;
   (C) washing and filtering the coprecipitated solution to obtain a solid catalyst;
   (D) drying the solid catalyst at 70~200° C.; and
   (E) heat-treating the dried solid catalyst at 350~800° C. to obtain the mixed manganese ferrite catalyst consisting of iron oxide ($\alpha$-$Fe_2O_3$), manganese iron oxide ($MnFeO_3$) and manganese ferrite ($MnFe_2O_4$).

2. The method of producing a mixed manganese ferrite catalyst according to claim 1,
   wherein the step (B) further comprises:
   stirring the aqueous precursor solution and alkaline solution for 6~12 hours such that coprecipitation is conducted.

3. The method of producing a mixed manganese ferrite catalyst according to claim 1, wherein the manganese precursor includes manganese chlorides or manganese nitrates, and the iron precursor includes iron chlorides or iron nitrates.

4. The method of producing a mixed manganese ferrite catalyst according to claim 3, wherein the iron precursor is selected from the group consisting of ferrous chloride tetrahydrate, ferrous chloride hexahydrate, ferrous chloride dihydrate, ferric chloride hexahydrate, ferrous nitrate hexahydrate, ferrous nitrate nonahydrate, ferric nitrate hexahydrate and ferric nitrate nonahydrate, and the manganese precursor is selected from the group consisting of manganous chloride, manganous chloride tetrahydrate, manganic chloride, manganese tetrachloride, manganese nitrate hexahydrate, manganese nitrate tetrahydrate and manganese nitrate monohydrate.

5. The method of producing a mixed manganese ferrite catalyst according to claim 1, wherein the step (B) is conducted at a temperature of 15~25° C.

6. The method of producing a mixed manganese ferrite catalyst according to claim 1, wherein the alkaline solution is a sodium hydroxide solution.

7. A mixed manganese ferrite catalyst produced using the method of claim 1, the catalyst having peaks in 2-theta ranges of 18.78~18.82, 24.18~24.22, 33.2~33.24, 35.64~35.68, 40.9~40.94, 45.22~45.26, 49.56~49.6, 54.22~54.26, 55.24~55.28, 57.92~57.96, 62.56~62.6, 64.04~64.08, 66.02~66.06, 72.16~72.2 and 75.78~75.82 in X-ray diffraction analysis.

8. A method of preparing 1,3-butadiene using a mixed manganese ferrite catalyst, comprising:
   (A) providing a mixed gas of a C4 mixture, air and steam as a reactant;
   (B) continuously passing the reactant through a catalyst layer supported with the catalyst produced using the method of claim 1 to conduct an oxidative dehydrogenation reaction, wherein said catalyst is the mixed manganese ferrite catalyst consisting of iron oxide ($\alpha$-$Fe_2O_3$), manganese iron oxide ($MnFeO_3$) and manganese ferrite ($MnFe_2O_4$); and
   (C) obtaining 1,3-butadiene from the catalyst layer.

9. The method of preparing 1,3-butadiene according to claim 8, wherein the C4 mixture comprises 0.5~50 wt % of n-butane, 40~99 wt % of n-butene, and 0.5~10 wt % of a balance of other constituents thereof.

10. The method of preparing 1,3-butadiene according to claim 8, wherein, in (A), a mixing molar ratio of n-butene:air:steam in the reactant is 1:0.5~10:1~50.

11. The method of preparing 1,3-butadiene according to claim 8, wherein, in (B), the oxidative dehydrogenation reaction is conducted at a reaction temperature of 300~600° C. and at a liquid hourly space velocity of 1~3 $h^{-1}$ based on n-butene.

* * * * *